US006207151B1

(12) United States Patent
Shimazaki et al.

(10) Patent No.: US 6,207,151 B1
(45) Date of Patent: Mar. 27, 2001

(54) AQUEOUS SOLUTION OF T-PA

(75) Inventors: Yukio Shimazaki; Nobuhiro Kawashima; Miki Suzuki; Yasuhito Tanaka, all of Mobara; Ryo Tanaka, Fujieda; Kiyoshi Sakai, Fujieda; Hisahiro Ishiwari, Fujieda, all of (JP)

(73) Assignee: Mitsui Chemicals Inc., Tokyo (JP)

( * ) Notice: Subject to any disclaimer, the term of this patent is extended or adjusted under 35 U.S.C. 154(b) by 0 days.

(21) Appl. No.: 08/259,152

(22) Filed: Jun. 13, 1994

Related U.S. Application Data

(63) Continuation of application No. 07/806,109, filed on Dec. 12, 1991, now abandoned, which is a continuation-in-part of application No. 07/580,922, filed on Sep. 12, 1990, now abandoned.

(30) Foreign Application Priority Data

Sep. 21, 1989 (JP) .................................................. 1-243311

(51) Int. Cl.$^7$ .................................................. A61K 38/49
(52) U.S. Cl. .................................... 424/94.63; 424/94.64; 424/94.1
(58) Field of Search ............................... 424/94.1, 94.63, 424/94.64; 435/219

(56) References Cited

U.S. PATENT DOCUMENTS

| 3,998,947 | * | 12/1976 | D'Hinterland et al. | ............ 424/94.1 |
|---|---|---|---|---|
| 4,083,961 | * | 4/1978 | Dussourd d'Hinterland | .... 424/94.64 |
| 4,314,994 | * | 2/1982 | Dussourd d'Hinterland et al. | ... 424/559 |
| 4,328,314 | * | 5/1982 | Horiguchi et al. | ................... 435/212 |
| 4,568,544 | * | 2/1986 | Hasegawa et al. | ................. 424/94.1 |
| 4,777,043 | * | 10/1988 | Bennett et al. | ................... 424/94.64 |
| 4,818,690 | * | 4/1989 | Pâques | ................................... 436/69 |
| 4,837,022 | * | 6/1989 | Kakimoto et al. | ................ 424/94.64 |
| 4,857,320 | * | 8/1989 | Wittwer | ............................. 424/94.63 |
| 4,929,560 | * | 5/1990 | Edmunds et al. | .................... 435/226 |
| 5,015,583 | * | 5/1991 | Pâques | ............................. 424/94.63 |
| 5,023,078 | * | 6/1991 | Halluin | ................................ 435/219 |
| 5,068,106 | * | 11/1991 | Pâques et al. | .................... 424/94.64 |
| 5,272,076 | * | 12/1993 | Burck et al. | ......................... 435/188 |

FOREIGN PATENT DOCUMENTS

0419252 * 9/1990 (EP) .

* cited by examiner

*Primary Examiner*—Irene Marx
(74) *Attorney, Agent, or Firm*—Nixon & Vanderhye

(57) ABSTRACT

Aqueous protein-containing solutions, in which a protein is dissolved at a high concentration at a pH near the isoelectric point of the protein by adding an anionic polymer or a salt thereof to the solution. Pharmaceutical formulations using a physiologically active protein are prepared using this technique.

1 Claim, No Drawings

AQUEOUS SOLUTION OF T-PA

This is a continuation of application Ser. No. 07/806,109, filed Dec. 12, 1991, now abandoned, which is a continuation in part of Ser. No. 07/580,922 filed Sep. 12, 1990 now abandoned.

BACKGROUND OF THE INVENTION

1. Field of the Invention

The present invention relates to protein-containing aqueous solutions, methods for increasing the protein concentration of aqueous solutions and a protein preparation and to techniques applicable in the preparation of pharmaceuticals for clinical use using physiologically active proteins.

2. Description of the Prior Art

In using a protein as a homogeneous component, it is extremely important to dissolve the protein in a solvent. For example, where a certain amount of a protein is fractionated from a composition which contains that protein or where analysis of the protein is made, the composition containing the protein must be homogeneous. Furthermore, when a protein is dissolved in water for administration as a pharmaceutical such as an injectable preparation, the protein has to be completely dissolved.

In general, the solubility of proteins in aqueous solvents is strongly affected by hydrophilic or hydrophobic residues present on the surface of the protein and by charges on the protein. When the protein is only slightly dissolved because of the presence of hydrophobic residues on the surface of the protein, it is possible to increase the solubility by adding a surfactant.

On the other hand, when the pH of an aqueous solvent is near the isoelectric point of the protein to be dissolved, which readily causes isoelectric precipitation, solubility of the protein can be increased by Increasing the salt concentration and the ionic strength of the aqueous solvent. In this case, a surfactant does not contribute to the increase of the protein solubility. Furthermore, when the pH of an aqueous solvent is near the isoelectric point of a protein and the salt concentration is low, the protein is soluble only at a relatively low concentration. Therefore, in order to dissolve the protein in a relatively high concentration, either a method in which a pH separate from the isoelectric point is used or a method in which the salt concentration is increased is generally used.

However, in some cases, It Is necessary to dissolve a protein at a sufficiently high concentration without increasing the salt concentration at the pH near the isoelectric point. An example is when a physiologically active protein having an isoelectric point near neutral pH is to be administered, in a form of a solution at a pH near neutral, to a patient who should maintain his or her salt Intake as low as possible. In this case, the only possible technique has been either to use the protein in a lower concentration or to inevitably administer salt, which is a serious practical problem to be solved in the formulation of protein active pharmaceuticals.

SUMMARY OF THE INVENTION

An object of the present invention is to provide a highly concentrated aqueous protein solution. Another object of the present invention is to provide a method in which a protein can be dissolved at a high concentration in an aqueous solution. Another object of the present invention Is to provide a protein preparation having excellent solubility.

In achieving the above objectives, the present inventors found that a protein present in a solution binds to an ion exchanger if the pH of the solution is appropriate, that the binding of the protein to the ion exchanger was prone to take place especially at a low salt concentration of the solution, and that the solubility of a complex of the protein and ion exchanger is much better than the solubility of the protein itself in the solution especially at a pH near the isoelectric point. This phenomenon resembles one in which a surfactant dissolves a hydrophobic protein by forming a complex of the protein and the surfactant.

Based on this finding, the present inventors additionally determined in the course of further investigations that anionic polymers or salts of anionic polymers exert a favorable effect mentioned above, and thus completed the present invention.

The present invention provides an aqueous solution containing a protein in which an anionic polymer or a salt thereof coexists with the protein; a method for increasing the protein concentration of an aqueous solution containing the protein by arranging an anionic polymer or a salt thereof to coexist with the protein; and a pharmaceutical composition containing an anionic polymer or a salt thereof and a protein.

A pharmaceutical preparation containing a saccharide, a type of anionic polymer, such as polysulfate or a sulfonated sugar and t-PA (tissue-type plasminogen activator) has been disclosed in Japanese Patent Laid-open No. 236730/1986. However, the disclosed technique is to improve t-PA activity and is fundamentally different, in terms of technological idea, from that of the present invention which more broadly is to improve the solubility of proteins in general.

The present invention enables a protein to dissolve in an aqueous solution, especially in an aqueous solution which has a low salt concentration and a pH near the isoelectric point of the protein, to a degree the conventional techniques have never been able to achieve.

Conventionally, in order to dissolve a protein at a pH near the protein's isoelectric point, it is essential to significantly (1) decrease the protein concentration or (2) increase the salt concentration. The resulting protein solution is extremely inconvenient when a physiologically active protein has to be administered in the form of a solution at a pH near the isoelectric point of the protein to a patient whose salt intake is restricted. In order to dissolve the protein without increasing the salt concentration, it is essential to select a pH separate from the pH near the isoelectric point of the protein even if the selected pH is undesirable for the use in pharmaceuticals such as injections or other parenteral dosage form.

By contrast, according to the present invention, proteins can be dissolved without increasing the salt concentration at a pH near the isoelectric point of the protein so that a protein-containing aqueous solution with a low salt concentration at a pH near the isoelectric point of the protein can be provided. The present Invention provides an advantageous technique as compared to conventional ones.

The present invention is particularly suitable for preparing low salt pharmaceutical preparations for injection of a physiologically active protein having an isoelectric point near neutral.

DETAILED DESCRIPTION AND THE PREFERRED EMBODIMENTS

Examples of proteins to be used in the present invention include physicochemically simple proteins. conjugated proteins and induced proteins as well as proteins having relatively large amounts of hydrophobic groups. In particular, this invention is suitably applied to proteins such as globulin or t-PA which tend to drastically decrease their solubility at a pH ranging around the isoelectric points. Examples include proteins having an isoelectric point apart from the extremely acid region, preferably pH 4 or higher, and desirably a pH 5 or higher. These proteins may be obtained by extraction and purification from naturally occurring biological bodies or parts thereof, by chemical synthesis or by using genetic recombinant DNA techniques from cell culture. The protein obtained as mentioned above can be used after modification. Examples of these proteins include gamma-globulins such as immunoglobulins A, G and E, lactoglobulin, urokinase, pro-urokinase and tissue-type plasminogen activator (t-PA). A more preferable example is t-PA having a solubility of 2.0 mg/ml or less and preferably 1.0 mg/ml or less, at a pH of about 7.3 in 1/15 M phosphate buffer. In particular, the present invention is specifically adapted for proteins having physiological activities.

The proteins can be used alone or as a mixture of two or more proteins or different types of proteins.

Examples of anion residues of anionic polymers used in the present invention include carboxyl, carboxymethyl, sulfuric and phosphoric groups. Examples of polymer backbones of the anionic polymers include sugars such as sugar alcohol, cellulose, amylose, amino acids and nucleic acid bases, preferably those having a molecular weight of 1,000–1,000,000 as the anionic polymer. Examples of the anionic polymers having both anion residues and polymer backbones are the carboxymethyl-ion-exchangers such as carboxymethylamylose and carboxymethylcellulose, acidic polysaccharides such as arginic acid, mucosaccharide sulfates such as dextran sulfate, chondroitin sulfate, chondroitin sulfate A, chondroitin sulfate B, chondroitin sulfate C, chondroitin sulfate D, chondroitin sulfate E, heparin, kerato sulfate, keratane sulfate and heparitine sulfate, acidic polyamino-acid such as poly-L-glutamic acid and nucleic acids. Illustrative salts of these anionic polymers include sodium, potassium, calcium and the like.

These anionic polymers can be used alone or in combination using two or more types.

The ratio of the anionic polymer or salt thereof to the protein to be dissolved is preferably 1/40 or more (w/w), desirably 1/10 to 100/1 (w/w), of that of a protein to be dissolved. If the amount of anionic polymer is not sufficient, the desired amount of protein dissolution may not be achieved; if the amount is excessive, the relative amount of protein to be dissolved is decreased, which prevents significant use of the protein-containing aqueous solution. Since anionic polymers and salts thereof are different from one another in the type of anionic residues, capability in exchanging cations, molecular weights and the like, the amounts of the anionic polymers and the salts thereof may be determined according to the physical properties of the protein to be formulated.

The concentration of the protein in a protein-containing aqueous solution attained by the present invention varies depending on the solubility of the protein to be dissolved. In practice, it is possible for the proteins exemplified above to dissolve in an aqueous solution at a protein concentration of at least 0.1 mg/ml since the solubility is significantly improved, especially at a pH near the isoelectric point, as compared with conventionally available concentrations. However, according to the present invention, protein precipitation does not occur over a wide range of protein concentration, even in a diluted solution. It is generally possible according to the present invention to prepare an aqueous solution with a protein concentration of approximately 0.01 to 10 mg/ml.

In the present Invention, the pH range of the aqueous solution is not particularly restricted. However, the present invention is characterized in that the solubility of the protein can be increased at a pH near the isoelectric point of the protein without increasing a salt concentration; considering the fact that the isoelectric point of a protein is mostly in the range between weakly acidic and alkaline pHs, the invention is particularly significant when the pH of the aqueous solution is in the range of weakly acidic, neutral, weakly alkaline or alkaline pHs. Specifically, the pH of the aqueous solution is preferably within the range of −2 to +2, preferably −1 to +1, pH units away from the isoelectric point of the protein.

In the present invention, the isoelectric point of the protein to be formulated is determined by electrophoresis. Further, in the case of protein, the isoelectric point is occasionally not converged into a point but appears as a band of a certain range of pH when determined by electrophoresis; in such a case, the pH range denotes the isoelectric point. Further, in a mixture of more than two proteins each having different isoelectric points, a pH range which covers isoelectric points of the all proteins denotes the isoelectric point of the protein mixture.

Ionic strength of an aqueous solution containing a protein and an anionic polymer or a salt thereof according to the present invention Is preferably 0.05 mol/l or less, more preferably 0.02 mol/l or less, particularly preferably 0. 01 mol/l or less. If the ionic strength exceeds 0.05 mol/l, the effect of the invention is readily lessened. This is probably because an interaction between the anionic residues of the anionic polymer and the protein is counteracted in the solution with high ionic strength.

Furthermore, the content of salts other than the anionic polymer or a salt thereof is preferably less than 0.1 mol per 1 mg protein. For example, in a solution with a high sodium chloride content, the effect due to the anionic polymer may be blocked.

In order to carry out the procedure of the present invention, the following method may be applied. First, a protein is dissolved at a pH apart from the isoelectric point and then to the resultant protein solution is added a solution containing an anionic polymer or its salt and the pH is adjusted to around the isoelectric point so as to prepare a solution in which the anionic polymer or the salt thereof coexists with the protein. Furthermore, another method is one in which an aqueous solution containing a protein and an anionic polymer or a salt thereof is prepared in advance at a pH apart from the isoelectric point of the protein and then the pH of the solution is readjusted near the isoelectric point of the protein.

In yet another method, a preparation containing a protein and an anionic polymer is prepared and then the preparation is dissolved. In order to produce such a preparation, any conventional method way be used. For example, a protein is dissolved in a diluted solution at a pH apart from the isoelectric point and then an anionic polymer aqueous solution is added to the solution. After pH adjustment, an excipient and the like are added to the solution, the resultant solution is filtered and dispensed into vials and then lyophilized to prepare a pharmaceutical preparation for injection. Alternatively, to protein aqueous solution is added an anionic polymer so as form a composite of the protein and the anionic polymer; the resulting composite is precipitated from in the solution by adjusting the pH to the isoelectric point of the composite, dried and then dispensed into vials after adding additives for formulation so as to prepare a preparation. Protein contents of the preparations are normally 0.01 to 50 wt. %.

If necessary, in order to prevent polymerization of the proteins and their adhesion to the containers, a surfactant such as TWEEN 80 (TWEEN sorbitan mono-9octadecenoate poly(oxy-1,2-ethanediyl) derivative, a chelating asent such as EDTA to eliminate the effect of metal ions on the protein, an agent to stabilize physiologically activity proteins, and furthermore an excipient such as mannitol and lactose (effective when used in a lyophilized preparation) may be added, besides an anionic polymer or a salt thereof, to a protein solution or a lyophilized product.

According to the present invention, a protein can be effectively dissolved without increasing the salt concentration or ionic strength at a pH near the isoelectric point. Conventional techniques have never been able to attain this. It is beyond the common knowledge of conventional dissolution techniques and is considered to be a significant advance in the art. The mechanism of the dissolution effect is not entirely evident; however, it is assumed that when an anionic polymer or a salt thereof is added to a solution at a pH near the isoelectric point of a protein, in which the solubility of the protein is extremely low by itself, the protein and the anionic polymer interact, particularly at low ionic strength, which results in an extreme increase in the solubility.

EXAMPLES

The present invention will be described more specifically in the following Examples.

Example 1

The protein used was human-derived tissue-type plasminogen activator (t-PA), which was obtained by expressing the structural gene of t-PA in cell culture using gene recombinant techniques then purifying and concentrating it from the culture fluid. The t-PA had been dissolved in a 60 mM sodium phosphate solution which was considered to be a sodium dihydrogen phosphate from its pH (4.2). 1 mg of t-PA and none 004 or 1.0 mg of the calcium salt of heparin were placed In a dialysis tube made of cellulose and then the total volume was made up to 1.0 ml with distilled water. Dialysis was carried out against 1,000 ml of a 1 mM citrate buffer solution for 3 hours. The fluid in the dialysis tube was transferred to a small polypropylene test tube, centrifuged at 15,000 rpm for 10 minutes and then the solubility of t-PA was determined by measuring the absorption at 280 nm of the supernatent. The isoelectric point of t-PA is about 6.5–7.5. The results are shown in Table 1 from which it is evident that the solubility of t-PA was improved by adding calcium heparin, particularly at pHs near the isoelectric point.

TABLE 1

| | Heparin (calcium salt) added | |
|---|---|---|
| pH | 0.04 | 0.0 |
| 4.0 | 0.15 | 0.10 |
| 4.8 | 0.38 | 0.43 |
| 5.5 | 0.50 | 0.56 |
| 6.0 | 0.89 | 0.99 |
| 7.0 | 0.88 | 0.99 |
| 7.5 | 0.89 | 0.99 |
| 8.0 | 0.86 | 0.99 |

Entries are solubility of t-PA (mg/ml)
a) Amount added per 1 mg of t-PA
b) pH corresponding to the isoelectric point of t-PA

Example 2

The solubility of t-PA was examined in the same manner as described in Example 1, except that various anionic polymers and cationic polymers shown in Table 2 were used in place of heparin in amounts of 0.1–0.2 mg. The pH of the solution was adjusted to about 7. The results are given in Table 2.

The solubility of t-PA was drastically increased in all cases with anionic polymers; however, no increase in solubility was observed with any of the cationic polymers. Furthermore, sufficient solubility was not attained oven with the addition of sodium chloride at high concentrations.

TABLE 2

| | Additives | |
|---|---|---|
| Name | Amount (mg/mg t-PA) | Solubility (mg/ml) |
| None | 0 | 0 |
| Anionic polymer | | |
| Poly-L-glutamic acid (sodium salt) | 0.1 | 1.02 |
| DNA (bacteria origin) | 0.18 | 0.99 |
| Dextran sulfate (calcium salt) | 0.1 | 1.03 |
| Heparin (calcium salt) | 0.1 | 1.04 |
| Chondroitin sulfate A (sodium salt) | 0.1 | 1.00 |
| Chondroitin sulfate B (sodium salt) | 0.1 | 1.01 |
| Chondroitin sulfate C (sodium salt) | 0.1 | 1.04 |
| Sodium arginic acid | 0.1 | 1.03 |
| Cationic polymer | | |
| Protamine sulfate | 0.1 | 0.00 |
| Poly-L-lysine | 0.1 | 0.01 |
| Salt | | |
| Sodium chloride | (200 mM) | 0.31 |

Example 3

The solubility of t-PA was examined In the same manner as described in Example 1, except that chondroitin sulfate A and heparan sulfate in amounts shown in Table 3 were used at pH about 7 in place of heparin. The results are shown In Table 3.

The study showed that t-PA solubility was improved particularly when the amount of chondroltin sulfate A and heparan sulfate were 1/40 or more of the t-PA by weight.

| Additive | Amount added (Ratio to t-PA by weight) | Solubility (mg/ml) |
|---|---|---|
| Chondroitin sulfate A (sodium salt) | 0 | 0.00 |
| | 1/40 | 0.51 |
| | 1/20 | 1.02 |
| | 3/40 | 1.03 |
| | 1/10 | 1.00 |
| Heparan sulfate (sodium salt) | 0 | 0.00 |
| | 1/40 | 0.20 |
| | 1/20 | 1.06 |

-continued

| Additive | Amount added (Ratio to t-PA by weight) | Solubility (mg/ml) |
|---|---|---|
| | 3/40 | 1.05 |
| | 1/10 | 1.05 |

Example 4

The pHs of aqueous solutions were adjusted to the isoelectric point of the individual proteins (t-PA and beta-lactoglobulin) and the solubilities of the proteins were examined with or without the addition of sodium chondroitin sulfate, the amount of which was one tenth of each protein. The results are shown In Table 4.

TABLE 4

| Protein | t-PA | Beta-lactoglobulin |
|---|---|---|
| Isoelectric points | 6.5–7.5 | 5.1 |
| pH of solution | 7 | 5 |
| Solubility (mg/ml) | | |
| Chondroitin sulfate − | 0.02 | <1.06 |
| Chondroitin sulfate + | 0.8 | 5.8 |

Example 5

| t-Pa | 100 mg |
|---|---|
| Sodium chondroitin sulfate | 10 mg |
| Lactose | 500 mg |

The above ingredients were dissolved in 25 ml of a 5 mm phosphate buffer solution (pH 7.0). After sterilization by filtration, the resultant solution was dispensed into vials, 2.5 ml each, and then lyophilized to prepare a t-PA preparation. This t-PA preparation could be re-dissolved in a 5% glucose infusion or distilled water for injection.

Example 6

| t-PA | 100 mg |
|---|---|
| Heparin (sodium salt) | 10 mg |
| Lactose | 500 mg |

The above ingredients were dissolved in 25 ml of a 5 mM phosphate buffer solution (pH 7.0). After sterilization by filtration, the resultant solution was dispensed into vials, 2.5 1 each, and then lyophilized to prepare a t-PA preparation. This t-PA preparation could be re-dissolved in a 5% glucose infusion or distilled water for injection.

Example 7

| t-PA | 100 mg |
|---|---|
| Dextrin sulfate (sodium salt) | 10 mg |
| Lactose | 500 mg |

The above ingredients were dissolved in 25 ml of a 5 mM phosphate buffer solution (pH 7.0). After sterilization by filtration, the resultant solution was dispensed into vials, 2.5 ml each, and then lyophilized to prepare a t-PA preparation. This t-PA preparation could be re-dissolved in a 5% glucose infusion or distilled water for injection.

What is claimed is:
1. The method for increasing the solubility of t-PA, in an aqueous solution at a pH of 5 to 9, said t-PA having a solubility of at most 2.0 mg/ml measured at a pH of about 7.3 in 1/15 M phosphate buffer said method comprising adding an anionic polymer or a salt thereof to said solution.

* * * * *